United States Patent [19]
Dalrymple

[11] Patent Number: 5,321,976
[45] Date of Patent: Jun. 21, 1994

[54] GOLF GREEN TEST APPARATUS

[76] Inventor: Donald D. Dalrymple, c/o Integra Trust Co. P.O. Box 189, Warren, Pa. 16365

[21] Appl. No.: 868,693

[22] Filed: Apr. 15, 1992

[51] Int. Cl.$^5$ .............................................. G01N 3/42
[52] U.S. Cl. .......................................... 73/81; 73/84; 73/85
[58] Field of Search ................... 73/81, 82, 83, 84, 85

[56] References Cited

U.S. PATENT DOCUMENTS

| | | | |
|---|---|---|---|
| 1,878,193 | 9/1932 | Scott et al. | 73/85 UX |
| 2,628,496 | 2/1953 | Wick | 73/818 |
| 3,282,094 | 11/1966 | Hinden | 73/85 X |
| 3,376,734 | 4/1968 | Ether | 73/78 |
| 3,894,588 | 7/1975 | Brill | 73/85 X |
| 3,968,428 | 7/1976 | Numoto | 324/694 |
| 4,136,554 | 1/1979 | Larson | 73/81 |
| 4,555,028 | 11/1985 | Velehrach | 73/78 X |
| 4,565,089 | 1/1986 | Arciszewski et al. | 73/85 X |
| 4,594,899 | 6/1986 | Henke et al. | 73/784 |
| 4,770,030 | 9/1988 | Smith | 73/84 |

FOREIGN PATENT DOCUMENTS

| | | | |
|---|---|---|---|
| 341512 | 10/1921 | Fed. Rep. of Germany | 73/85 |
| 417104 | 8/1925 | Fed. Rep. of Germany | 73/85 |

*Primary Examiner*—Tom Noland
*Attorney, Agent, or Firm*—E. Michael Combs

[57] ABSTRACT

A resiliency and relative hardness of a golf green is tested by the apparatus having a support base mounting a measuring rod orthogonally oriented relative to the support base and coaxially aligned with a support base bore. A golf ball sphere slidably directed through the bore and its resistance effected by contact with an underlying golf green is measured by relative projection of the sphere within the golf green and simultaneous deflection of a dial indicator foot measuring projection of the golf ball sphere into the golf green.

3 Claims, 4 Drawing Sheets

GOLF GREEN TEST APPARATUS

BACKGROUND OF THE INVENTION

1. Field of the Invention

The field of invention relates to measuring apparatus, and more particularly pertains to a new and improved golf green test apparatus wherein the same is arranged to measure relative penetration of a golf ball into an underlying golf green.

2. Description of the Prior Art

In the care and maintenance of golf greens, a green that has not been watered sufficiently will not accommodate golf balls and back-spin imparted to such golf balls in a proper manner, wherein a golf green having been saturated with too much water will not properly react to a golf ball, wherein accordingly the proper amount of watering of a golf green is measured by the instant invention providing for relative penetration of a golf green surface by an associated golf ball sphere. Prior art swivel testing organizations are available in the prior art, but are not directly related to golf green care maintenance and exemplified in U.S. Pat. No. 4,770,030 to Smith effecting relative swivel penetration testing.

U.S. Pat. No. 3,894,588 to Brill sets forth a swivel testing apparatus measuring static friction of soils.

A portable soil moisture tester is set forth in U.S. Pat. No. 3,968,428 to Munoto, and U.S. Pat. No. 4,594,899 to Henkel, et al. sets forth measurement and testing of liquefacation resistance and soil degradation.

As such, it may be appreciated that there continues to be a need for new and improved golf green test apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of soil testing apparatus now present in the prior art, the present invention provides a golf green test apparatus wherein the same is arranged to measure respective penetration of a golf ball sphere relative to a golf green. As such, the general purpose of the present invention, which will be described subsequently in greater detail, is to provide a new and improved golf green test apparatus which has all the advantages of the prior art soil test apparatus and none of the disadvantages.

To attain this, a resiliency and relative hardness of a golf green is tested by the apparatus having a support base mounting a measuring rod orthogonally oriented relative to the support base and coaxially aligned with a support base bore. A golf ball sphere slidably directed through the bore and its resistance effected by contact with an underlying golf green is measured by relative projection of the sphere within the golf green and simultaneous deflection of a dial indicator foot measuring projecting of the golf ball sphere into the golf green.

It is therefore an object of the present invention to provide a new and improved golf green test apparatus which has all the advantages of the prior art soil test apparatus and none of the disadvantages.

It is another object of the present invention to provide a new and improved golf green test apparatus which may be easily and efficiently manufactured and marketed.

It is a further object of the present invention to provide a new and improved golf green test apparatus which is of a durable and reliable construction.

An even further object of the present invention is to provide a new and improved golf green test apparatus which is susceptible of a low cost of manufacture with regard to both materials and labor, and which accordingly is then susceptible of low prices of sale to the consuming public, thereby making such golf green test apparatus economically available to the buying public.

Still yet another object of the present invention is to provide a new and improved golf green test apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be has to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
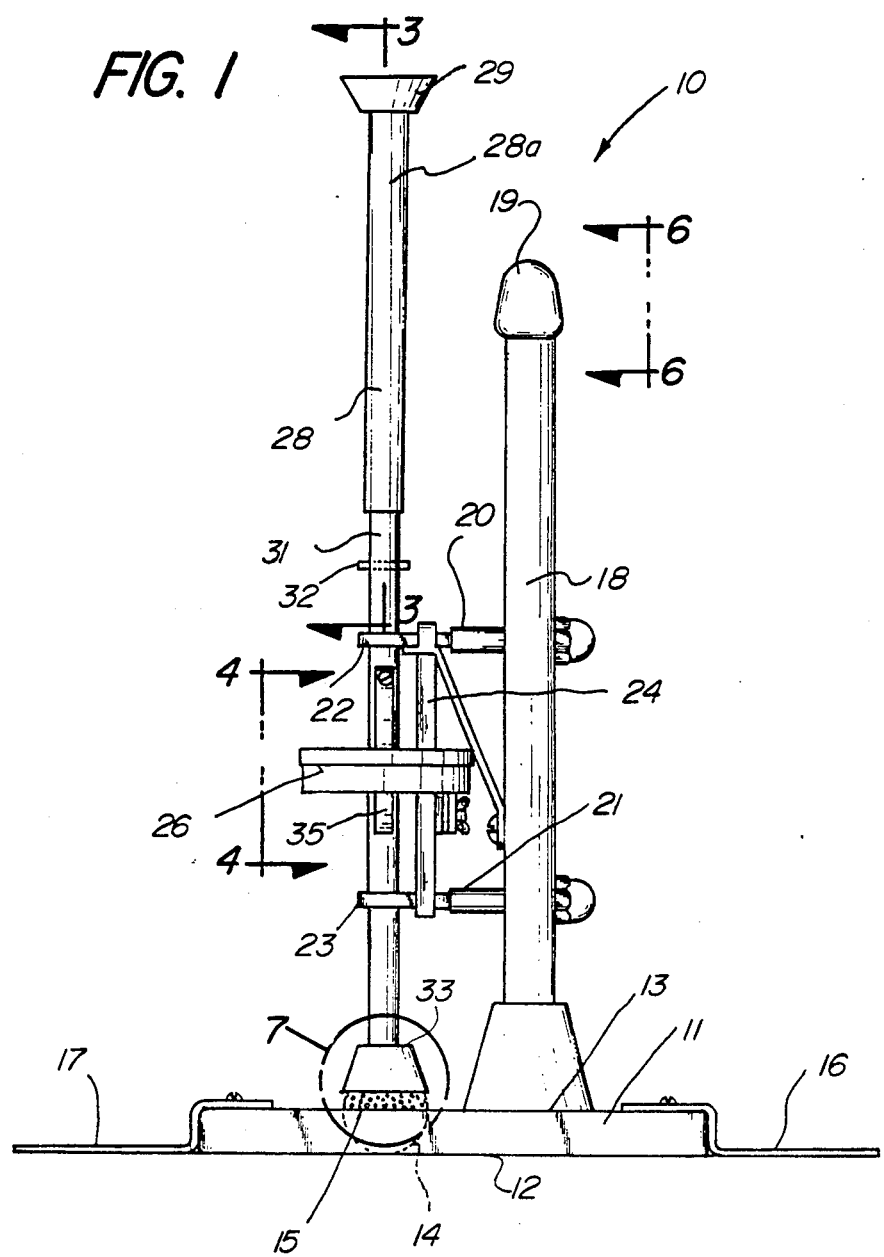
FIG. 1 is an orthographic view, taken in elevation, of the invention.
Figure 2:
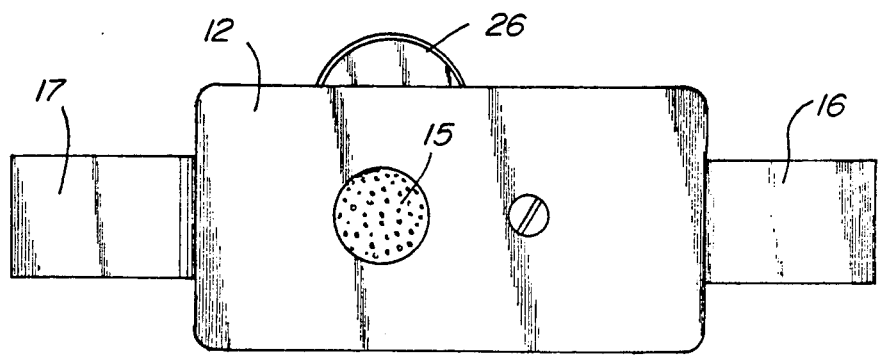
FIG. 2 is an orthographic bottom view of the instant invention.
Figure 3:
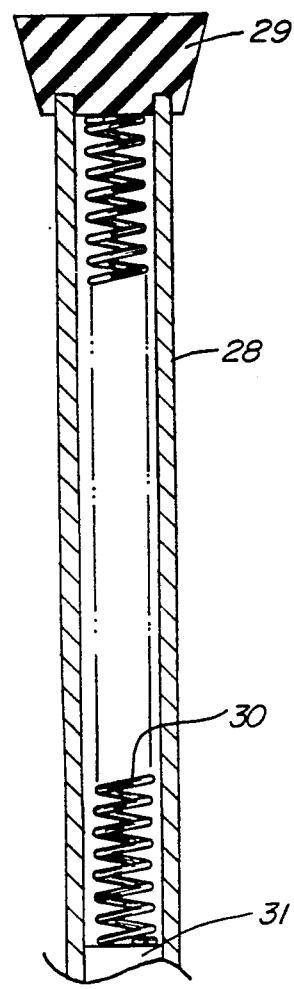
FIG. 3 is an orthographic view, taken along the lines 3—3 of FIG. 1 in the direction indicated by the arrows.

With reference now to the drawings, and in particular to FIGS. 1 to 8 thereof, a new and improved golf green test apparatus embodying the principles and concepts of the present invention and generally designated by the reference numeral 10 will be described.

More specifically, the golf green test apparatus 10 of the instant invention essentially comprises a support base 11 having a bottom wall 12 spaced from and parallel a top wall 13. A support base bore 14 is orthogonally directed through the support base form the bottom wall 12 through the top wall 13, with a golf ball sphere 15 mounted within the bore 14 in a slidable relationship therethrough in a first position tangentially aligned relative to the bottom wall 12. A support rod 18 orthogonally mounted to the top wall 13 spaced from the bore 14 extends upwardly therefrom terminating in a handle loop 19 arranged for ease of transport of the organization during use. The support rod 18 includes an upper and lower support beam 20 and 21 respectively orthogonally mounted to the support rod in a parallel relationship relative to one another, wherein the upper support beam 20 includes an upper guide loop 22, with the lower support beam 21 having a lower guide loop 23, wherein the upper and lower guide loops are coaxially aligned relative to one another whose axis is coincident with an axis of the bore 14. The upper and lower support beams include a support member 24 orthogonally directed between the upper and lower support beams 20 and 21, with the support member 24 including a support member mounting leg 25 orthogonally oriented relative to the support member 24, wherein the mounting leg 25 secures a dial indicator 26 thereto, with the dial indicator having a dial indicator foot 27 reciprocatably mounted relative to the dial indicator as a means of measuring displacement of the dial indicator foot 27, with the dial indicator foot 27 orthogonally oriented relative to a support sleeve axis 28a of a support sleeve 28 having a measuring rod 31 slidingly and telescopingly received within the support sleeve through a lower distal end thereof, wherein the support sleeve includes a support sleeve spring 30 mounted and captured between the measuring rod 31 and an upper distal end of the support sleeve 28. The support sleeve includes a support sleeve handle 29 mounted to an upper distal end of the support sleeve to permit ease of displacement downwardly of the support sleeve. Upon downward displacement of the support sleeve, the spring 30 is compressed and effects deflection of the measuring rod 31 downwardly as the measuring rod 31 is slidingly and guidingly aligned within the upper and lower guide loops 22 and 23 and coaxially aligned relative to the axis 28a. Its lower terminal end includes a mounting cup 33 having a semi-spherical recess 34 whose axis is coincident with the axis 28a, with the golf ball sphere 15 adherably mounted within the semi-spherical recess 34. A measuring rod abutment leg 32 mounted to the measuring rod above the upper guide loop 22 and below the support sleeve 28 is spaced in a first position above the upper guide loop 22 a predetermined spacing to permit and effect equal downward displacement and compression of the spring 30 when the support sleeve 28 is projected downwardly in varying tests of an underlying golf green to provide for a readily repeatable testing of the golf green surface.

Figure 4:
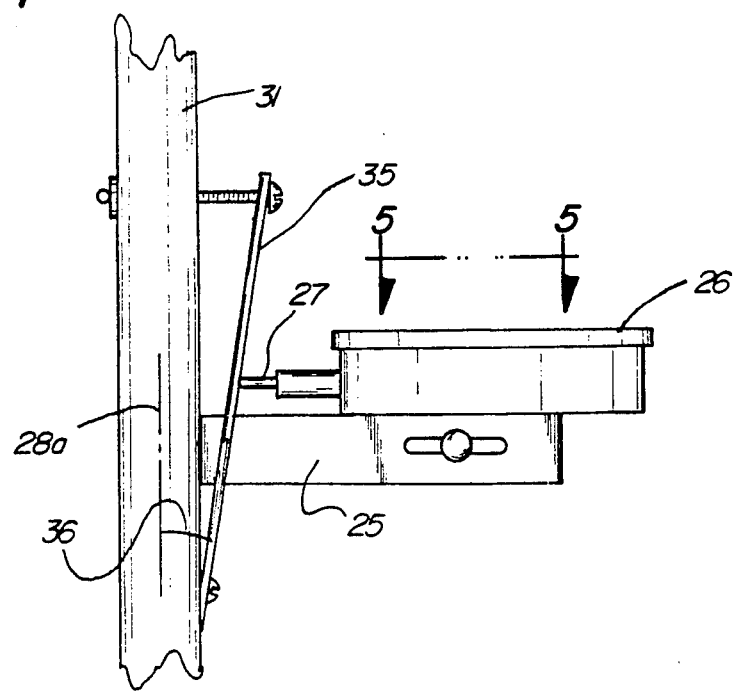
FIG. 4 is an orthographic view, taken along the lines 4—4 of FIG. 1 in the direction indicated by the arrows.
Figure 5:
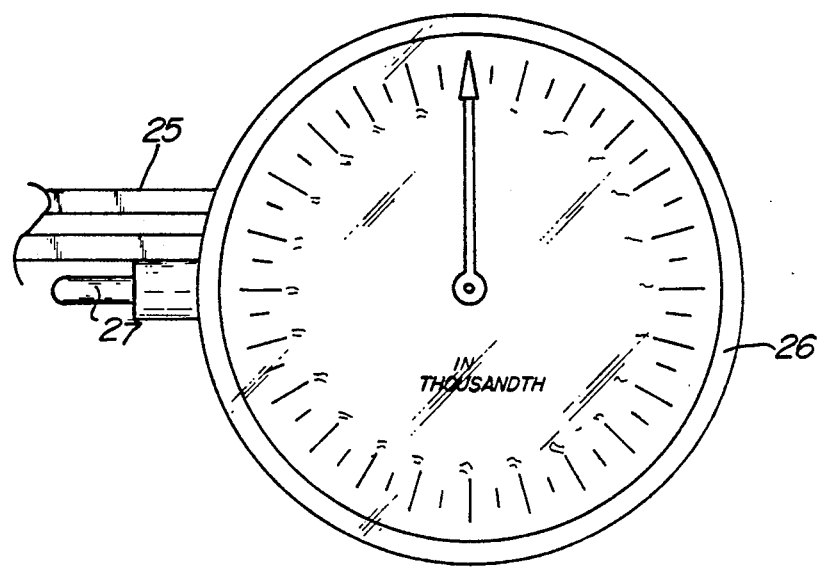
FIG. 5 is an orthographic view, taken along the lines 5—5 of FIG. 4 in the direction indicated by the arrows.
Figure 6:
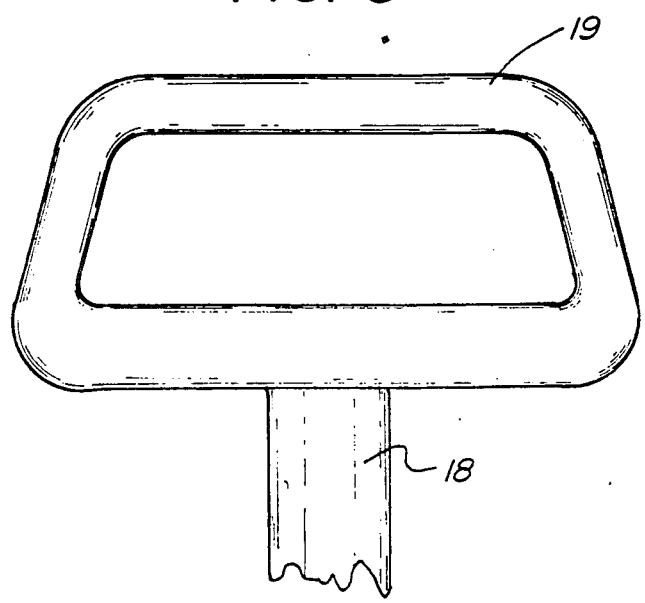
FIG. 6 is an orthographic view, taken along the lines 6—6 of FIG. 1 in the direction indicated by the arrows.
Figure 7:
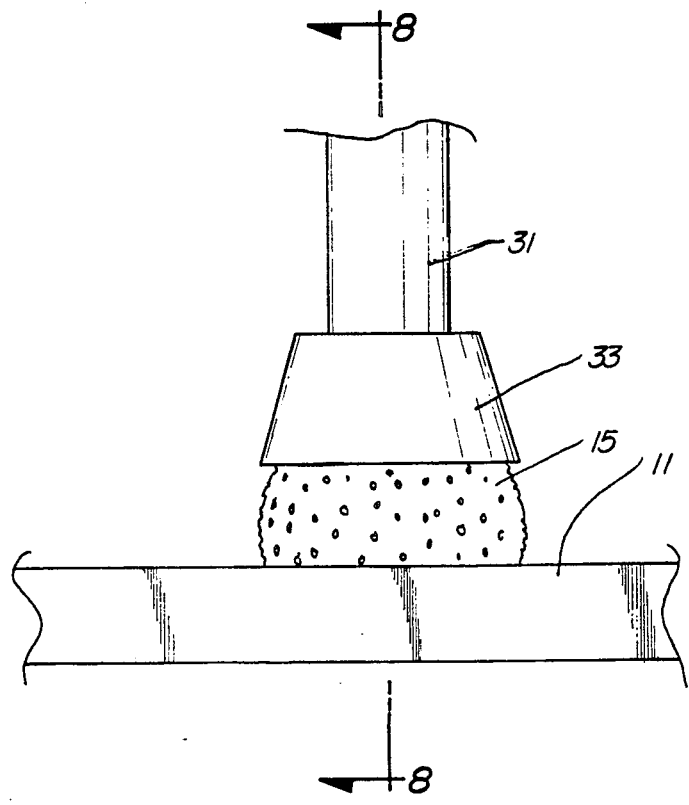
FIG. 7 is an orthographic view if section 7, as set forth in FIG. 1.
Figure 8:
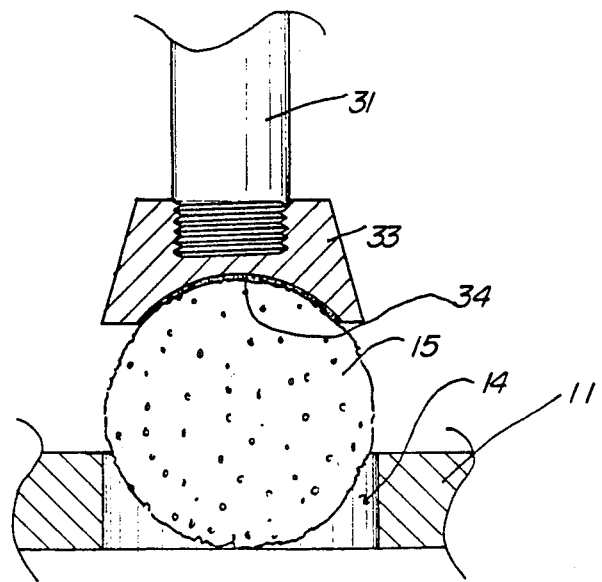
FIG. 8 is an orthographic view, taken along the lines 8—8 of FIG. 7 in the direction indicated by the arrows.

An abutment plate 35 is mounted adjacent the measuring rod 31 and positioned between the measuring rod 31 and the dial indicator foot 27 in abutment with the dial indicator foot 27 as the abutment plate 35 is canted upwardly relative to the measuring rod 31 to define an acute included angle relative to a lower distal end of the abutment plate 35 and the axis 28a, whereupon downward projection of the measuring rod effects horizontal displacement of the dial indicator foot 27, in a manner as illustrated in the FIG. 4 for example.

It should be further noted that the first and second flanges 16 and 17 in their coplanar relationship relative to the bottom wall 12 are arranged on opposed sides of the base for receiving an individual's feet thereon to secure the apparatus overlying a golf green for stability of the apparatus in projecting the measuring rod and the associated golf ball sphere into the golf green.

As to the manner of usage and operation of the instant invention, the same should be apparent form the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A golf green test apparatus, comprising:
  a support base, the support base including a bottom wall, spaced from, parallel to, and coextensive with a top wall;
  a bore directed orthogonally through the support base from the bottom wall through the top wall;
  a golf ball sphere slidably mounted within the bore extensible from a first position tangentially aligned with the bottom wall to a second position projecting below the bottom wall;
  drive means for projecting the golf ball sphere from the first position to the second position;
  the drive means including a measuring rod, the measuring rod orthogonally oriented relative to the top wall, the measuring rod having a mounting cup mounted at a lower distal end thereof, the mounting cup having the golf ball sphere fixedly secured therewithin, wherein the measuring rod, the mounting cup, and the golf ball sphere are coaxially aligned relative to the bore,
  and
  the drive means further including a support sleeve, the support sleeve telescopingly receiving the measuring rod therewithin, the support sleeve having a support sleeve handle at an upper distal end of the support sleeve, and a spring captured between the support sleeve handle and the measuring rod;
  and
  a support rod, the support rod arranged in a parallel spaced relationship relative to the measuring rod and the support sleeve, the support rod fixedly secured to the top wall, and including an upper support beam spaced from and parallel to a lower support beam, where the upper support beam and the lower support beam are orthogonally oriented relative to the support rod, the upper support beam includes an upper guide loop, the lower support beam includes a lower guide loop, wherein the upper guide loop and the lower guide loop are coaxially aligned relative to the bore, spaced above the bore, and positioned below the support sleeve, with the measuring rod slidably received through the upper guide loop and the lower guide loop, with the measuring means arranged for measuring displacement of the measuring rod past the measuring means, wherein the measuring means includes a measuring foot, with the measuring foot reciprocably mounted relative to the measuring means, and the foot orthogonally oriented relative to the measuring rod, the measuring rod further including an abutment plate fixedly mounted to the measuring rod between the upper guide loop and the lower guide loop, with the abutment plate canted upwardly relative to the measuring rod defining an acute angle between the measuring rod and the abutment plate.

2. An apparatus as set forth in claim 1 wherein the support rod includes a handle loop mounted to an upper distal end of the support rod for ease of transport of the apparatus.

3. An apparatus as set forth in claim 2 including a first flange and a second flange mounted to the support base projecting laterally therefrom, wherein the first flange and the second flange are coplanar with the bottom wall.

* * * * *